(12) United States Patent
Chen et al.

(10) Patent No.: US 10,366,274 B2
(45) Date of Patent: Jul. 30, 2019

(54) FINGERPRINT IDENTIFICATION SYSTEM, FINGERPRINT IDENTIFICATION METHOD, AND ELECTRONIC EQUIPMENT

(71) Applicant: BYD COMPANY LIMITED, Shenzhen (CN)

(72) Inventors: Guilan Chen, Shenzhen (CN); Qiyong Wen, Shenzhen (CN); Tiejun Cai, Shenzhen (CN); Bangjun He, Shenzhen (CN); Yun Yang, Shenzhen (CN)

(73) Assignee: BYD COMPANY LIMITED, Shenzhen (CN)

( * ) Notice: Subject to any disclaimer, the term of this patent is extended or adjusted under 35 U.S.C. 154(b) by 193 days.

(21) Appl. No.: 15/537,707

(22) PCT Filed: Nov. 3, 2015

(86) PCT No.: PCT/CN2015/093728
§ 371 (c)(1),
(2) Date: Jun. 19, 2017

(87) PCT Pub. No.: WO2016/095615
PCT Pub. Date: Jun. 23, 2016

(65) Prior Publication Data
US 2018/0005014 A1    Jan. 4, 2018

(30) Foreign Application Priority Data
Dec. 19, 2014 (CN) .......................... 2014 1 0799636

(51) Int. Cl.
*G06K 9/00* (2006.01)
*A61B 5/1172* (2016.01)

(52) U.S. Cl.
CPC ........ *G06K 9/00087* (2013.01); *A61B 5/1172* (2013.01); *G06K 9/0002* (2013.01); *G06K 9/00026* (2013.01)

(58) Field of Classification Search
None
See application file for complete search history.

(56) References Cited

U.S. PATENT DOCUMENTS

| 6,567,539 | B1 * | 5/2003 | Benezeth | G06K 9/00013 356/71 |
| 2003/0123714 | A1 * | 7/2003 | O'Gorman | G06K 9/00026 382/124 |

(Continued)

FOREIGN PATENT DOCUMENTS

| CN | 1172308 A | 2/1998 |
| CN | 1617161 A | 5/2005 |

(Continued)

OTHER PUBLICATIONS

The World Intellectual Property Organization (WIPO) International Search Report for PCT/CN2015/093728 dated Jan. 27, 2016 pp. 1-6.

(Continued)

*Primary Examiner* — Randolph I Chu
(74) *Attorney, Agent, or Firm* — Anova Law Group, PLLC

(57) ABSTRACT

In the fingerprint identification system according to the present disclosure, the fingerprint sensor collects multiple frames of fingerprint images sliding-inputted by a user, the judging unit determines whether, among the multiple frames of fingerprint images, there is a first overlap region between a current frame of fingerprint images and a previous frame of fingerprint images; if yes, the judging unit removes the first overlap region from the current frame of fingerprint images and superposes the previous frame of fingerprint images with the current frame of fingerprint images to form a superposed fingerprint image; the judging unit completes judgment of all the multiple frames of fingerprint images to obtain a template fingerprint image; the processing unit (Continued)

saves characteristic points of the complete template fingerprint image. The fingerprint sensor collects a to-be-identified fingerprint image pressing-inputted by the user, and the processing unit determines whether the characteristic points of the to-be-identified fingerprint image match with the characteristic points of the template fingerprint image. When establishing template fingerprint database, the fingerprint identification system collects the fingerprint sliding-inputted by the user and the to-be-identified fingerprint pressing-inputted by the user in the subsequent matching process. Therefore, the input and identification efficiency is much higher than that of existing methods. The present disclosure also provides a fingerprint identification method and an electric equipment.

12 Claims, 6 Drawing Sheets

(56) References Cited

U.S. PATENT DOCUMENTS

| | | | | |
|---|---|---|---|---|
| 2003/0138136 | A1* | 7/2003 | Umezaki | G06K 9/00006 |
| | | | | 382/124 |
| 2005/0129291 | A1* | 6/2005 | Boshra | G06K 9/00026 |
| | | | | 382/124 |
| 2006/0182319 | A1* | 8/2006 | Setlak | G06K 9/00026 |
| | | | | 382/124 |
| 2007/0165913 | A1* | 7/2007 | Tyan | G06K 9/00026 |
| | | | | 382/124 |
| 2013/0076880 | A1* | 3/2013 | Saxena | G06K 9/00026 |
| | | | | 348/77 |
| 2014/0086460 | A1 | 3/2014 | Bechtel | |
| 2014/0294261 | A1* | 10/2014 | Abe | G06K 9/00006 |
| | | | | 382/124 |
| 2015/0086090 | A1* | 3/2015 | Jung | G06K 9/00013 |
| | | | | 382/124 |
| 2015/0347809 | A1* | 12/2015 | Christie | G06K 9/0004 |
| | | | | 382/124 |
| 2016/0034738 | A1* | 2/2016 | Luo | G06K 9/001 |
| | | | | 382/125 |

FOREIGN PATENT DOCUMENTS

| | | |
|---|---|---|
| CN | 1804862 A | 7/2006 |
| CN | 101005353 A | 7/2007 |
| CN | 101079087 A | 11/2007 |
| CN | 101145198 A | 3/2008 |
| CN | 104156709 A | 11/2014 |
| EP | 2141633 A2 | 1/2010 |
| JP | 2003331269 A | 11/2003 |
| WO | 03007127 A2 | 1/2003 |

OTHER PUBLICATIONS

The European Patent Office (EPO) Supplementary European Search Report for Application No. 15869125.3 dated Nov. 3, 2017 3 Pages.
Moon, Y.S. et al, "Template Synthesis and Image Mosaicking for Fingerprint Registration: An Experimental Study" The Chinese University of Hong Kong, Department of Computer Science and Engineering, ICASSP 2004, pp. V409-V412.

* cited by examiner

FINGERPRINT IDENTIFICATION SYSTEM, FINGERPRINT IDENTIFICATION METHOD, AND ELECTRONIC EQUIPMENT

CROSS REFERENCE TO RELATED APPLICATION

This application is a national phase entry under 35 U.S.C. § 371 of International Application No. PCT/CN2015/093728, filed on Nov. 3, 2015, which claims priority and benefits of Chinese Patent Application No. 201410799636.7, filed with State Intellectual Property Office, P. R. C. on Dec. 19, 2014, the entire content of which is incorporated herein by reference.

FIELD

Embodiments of the present disclosure generally relate to a fingerprint identification technology, and, more particularly, to a fingerprint identification system, a fingerprint identification method, and an electronic equipment.

BACKGROUND

Currently, area fingerprint sensors are using a pressing-style input method. When inputting, the finger presses on a fingerprint sensor, the fingerprint sensor can obtain fingerprint information of the pressed part of the finger at once, and there is no need to move the finger. However, because the area of the fingerprint scanning module is limited, the fingerprint sensor detects a relatively small area of the finger every time the finger presses, and relatively complete fingerprint information can be obtained by inputting several times.

At the same time, due to the structural limitation, or for better appearance, the fingerprint scanning module of the fingerprint sensor may become smaller and smaller. When collecting a fingerprint, the fingerprint sensors collect less and less information from each pressing, and the finger needs to press on the fingerprint sensor for several times to ensure that the fingerprint sensor can collect enough characteristic points for subsequent matching processes. Thus, the collecting process for a fingerprint database is tedious and very time consuming.

SUMMARY

The present disclosure seeks to solve at least one of the technical problems in the related art to some extent. Therefore, the present disclosure provides a fingerprint identification system, a fingerprint identification method, and an electric equipment.

The fingerprint identification system includes a fingerprint sensor, a judging unit and a processing unit, and:

the fingerprint sensor collects multiple frames of fingerprint images sliding-inputted by a user;

the judging unit determines whether, among the multiple frames of fingerprint images, there is a first overlap region between a current frame of fingerprint images and a previous frame of fingerprint images;

when there is a first overlap region between a current frame of fingerprint images and a previous frame of fingerprint images, the judging unit removes the first overlap region from the current frame of fingerprint images and superposes the previous frame of fingerprint images with the current frame of fingerprint images without the first overlap region thereof to form a superposed fingerprint image; or the judging unit removes the first overlap region from the previous frame of fingerprint images and superposes the current frame of fingerprint images with the previous frame of fingerprint images without the first overlap region to form the superposed fingerprint image;

the judging unit also judges whether there is a second overlap region between a next frame of fingerprint images and the superposed fingerprint image, until completing judgment of all the multiple frames of fingerprint images to obtain a template fingerprint image;

when there is not a first overlap region between a current frame of fingerprint images and a previous frame of fingerprint images, the fingerprint sensor collects new multiple frames of fingerprint images sliding-inputted by the user;

the processing unit extracts and saves characteristic points of the complete template fingerprint image;

the fingerprint sensor collects a to-be-identified fingerprint image pressing-inputted by the user, and the processing unit extracts characteristic points of the to-be-identified fingerprint image and determines whether the characteristic points of the to-be-identified fingerprint image match with the characteristic points of the template fingerprint image;

when the characteristic points of the to-be-identified fingerprint image match with the characteristic points of the template fingerprint image, the processing unit determines the to-be-identified fingerprint image as a matching fingerprint image; and when the characteristic points of the to-be-identified fingerprint image do not match with the characteristic points of the template fingerprint image, the processing unit determines the to-be-identified fingerprint image as a non-matching fingerprint image.

According to the fingerprint identification system, when establishing the template fingerprint database, the fingerprint sensor can be used to collect the multiple frames of fingerprint images sliding-inputted by the user, and the judging unit superposes the sliding-inputted frames together using an image-stitching technique. Thus, the amount of information collected by the fingerprint sensor for each sliding-input is much more than the amount of information collected by the fingerprint sensor for each pressing-input under existing methods, and the input efficiency is much higher than that of existing methods. The inputting process can be completed by one-time collection of the left side, middle side, and right side of the finger, respectively, and is convenient to input, avoiding complex operations and improving user experience. In the subsequent matching process, the user presses the finger on the fingerprint sensor, and the fingerprint sensor can collect the fingerprint of the pressed-part of the finger, and the processing unit can compare the collected fingerprint with template fingerprint database. It is possible that the user uses regular angles when inputting the fingerprints, but the matching process can still be successful at various angles.

In one embodiment, the processing unit is configured to perform filtering, binarization, and thinning processing on the template fingerprint image, and to extract the characteristic points of the template fingerprint image.

In one embodiment, the previous frame of fingerprint images includes the previous frame image part, the current frame of fingerprint images includes a plurality of current frame image parts, and the judging unit respectively calculates gray differences between the first gray scale of the previous frame image part and corresponding second gray scales of the plurality of the current frame image parts to obtain a plurality of the gray scale differences, and to compare the plurality of the gray scale differences; and when a gray scale difference between a second gray scale and the first gray scale is a minimum gray scale difference among the plurality of the gray scale differences, and the minimum gray scale deference is smaller than a first threshold, the judging unit is configured to determine the current frame image part corresponding to the second gray scale as the first overlap region.

In one embodiment, the previous frame of fingerprint images includes the previous frame image part, the current frame of fingerprint images includes groups of a plurality of current frame image parts, and each group of the plurality of current frame image parts includes a first current frame image part, a second current frame image part, and a third current frame image part;

the judging unit is configured to calculate a first gray scale difference between a first gray scale of the previous frame image part and a first gray scale of the first current frame image part of one group of current frame image parts, a second gray scale difference between the first gray scale of the previous frame image part and a second gray scale of the second current frame image part of the one group of current frame image parts, and a third gray scale difference between the first gray scale of the previous frame image part and a third gray scale of the third current frame image part of the one group of current frame image parts, respectively, to obtain a gray scale sum of the first gray scale difference, the second gray scale difference and the third gray scale difference and, after a plurality of gray scale sums are obtained, to compare the plurality of gray scale sums;

when the gray scale sum of a group of current frame image parts has a minimum value among the plurality of the gray scale sums, the judging unit compares the first gray scale difference, the second gray scale difference, and the third gray scale difference corresponding to the one group of current frame image parts; and when a value of a gray scale difference is minimum among the group and the value is less than a second threshold, the judging unit determines the current frame image part corresponding to the gray scale difference having the minimum value as the first overlap region.

A method of fingerprint identification includes the steps of:

S1: collecting, by a fingerprint sensor, multiple frames of fingerprint images sliding-inputted by a user S2: judging, by a judging unit, whether, among the multiple frames of fingerprint images, there is a first overlap region between a current frame of fingerprint images and a previous frame of fingerprint images; when there is a first overlap region between a current frame of fingerprint images and a previous frame of fingerprint images, proceeding to S3; and when there is not a first overlap region between a current frame of fingerprint images and a previous frame of fingerprint images, returning to S1;

S3: removing, by the judging unit, the first overlap region from the current frame of fingerprint images and superposing the previous frame of fingerprint images with the current frame of fingerprint images without the first overlap region thereof to form a superposed fingerprint image; or removing, by the judging unit, the first overlap region from the previous frame of fingerprint images and superposing the current frame of fingerprint images with the previous frame of fingerprint images without the first overlap region to form the superposed fingerprint image;

S4: judging, by the judging unit, whether there is a second overlap region between a next frame of fingerprint images and the superposed fingerprint image, until completing judgment of all the multiple frames of fingerprint images to obtain a template fingerprint image;

S5: extracting and saving, by a processing unit, characteristic points of the complete template fingerprint image;

S6: collecting, by the fingerprint sensor, a to-be-identified fingerprint image pressing-inputted by the user;

S7: extracting, by the processing unit, characteristic points of the to-be-identified fingerprint image and determining whether the characteristic points of the to-be-identified fingerprint image match with the characteristic points of the template fingerprint image; when the characteristic points of the to-be-identified fingerprint image match with the characteristic points of the template fingerprint image, proceeding to S8; and when the characteristic points of the to-be-identified fingerprint image do not match with the characteristic points of the template fingerprint image, proceeding to S9;

S8: determining, by the processing unit, the to-be-identified fingerprint image as a matching fingerprint image; and S9: determining, by the processing unit, the to-be-identified fingerprint image as a non-matching fingerprint image.

In one embodiment, Step S5 further comprises: performing, by, the processing unit filtering, binarization, and thinning processing on the template fingerprint image to extract the characteristic points of the template fingerprint image.

In one embodiment, the previous frame of fingerprint images includes the previous frame image part, the current frame of fingerprint images includes a plurality of current frame image parts, and Step S2 further comprises:

respectively calculating, by the judging unit, gray differences between the first gray scale of the previous frame image part and corresponding second gray scales of the plurality of the current frame image parts to obtain a plurality of the gray scale differences, and comparing the plurality of the gray scale differences; and when a gray scale difference between a second gray scale and the first gray scale is a minimum gray scale difference among the plurality of the gray scale differences, and the minimum gray scale deference is smaller than a first threshold, determining, by the judging unit, the current frame image part corresponding to the second gray scale as the first overlap region.

In one embodiment, the previous frame of fingerprint images includes the previous frame image part, the current frame of fingerprint images includes groups of a plurality of current frame image parts, and each group of the plurality of current frame image parts includes a first current frame image part, a second current frame image part, and a third current frame image part; and Step S2 further comprises:

calculating, by the judging unit, a first gray scale difference between a first gray scale of the previous frame image part and a first gray scale of the first current frame image part of one group of current frame image parts, a second gray scale difference between the first gray scale of the previous frame image part and a second gray scale of the second current frame image part of the one group of current frame image parts, and a third gray scale difference between the first gray scale of the previous frame image part and a third gray scale of the third current frame image part of the one group of current frame image parts, respectively, to obtain a gray scale sum of the first gray scale difference, the second gray scale difference and the third gray scale difference and, after a plurality of gray scale sums are obtained, comparing the plurality of gray scale sums;

when the gray scale sum of a group of current frame image parts has a minimum value among the plurality of the gray scale sums, comparing, by the judging unit, the first gray scale difference, the second gray scale difference, and the third gray scale difference corresponding to the one group of current frame image parts; and when a value of a gray scale difference is minimum among the group and the value is less than a second threshold, determining, by the judging unit, the current frame image part corresponding to the gray scale difference having the minimum value as the first overlap region.

An electric equipment includes a fingerprint identification system, the fingerprint identification system includes a fingerprint sensor, a judging unit and a processing unit, and the fingerprint sensor collects multiple frames of fingerprint images sliding-inputted by a user;

the judging unit determines whether, among the multiple frames of fingerprint images, there is a first overlap region between a current frame of fingerprint images and a previous frame of fingerprint images;

when there is a first overlap region between a current frame of fingerprint images and a previous frame of fingerprint images, the judging unit removes the first overlap region from the current frame of fingerprint images and superposes the previous frame of fingerprint images with the current frame of fingerprint images without the first overlap region thereof to form a superposed fingerprint image; or the judging unit removes the first overlap region from the previous frame of fingerprint images and superposes the current frame of fingerprint images with the previous frame of fingerprint images without the first overlap region to form the superposed fingerprint image;

the judging unit also judges whether there is a second overlap region between a next frame of fingerprint images and the superposed fingerprint image, until completing judgment of all the multiple frames of fingerprint images to obtain a template fingerprint image;

the processing unit extracts and saves characteristic points of the complete template fingerprint image;

when there is not a first overlap region between a current frame of fingerprint images and a previous frame of fingerprint images, the fingerprint sensor collects new multiple frames of fingerprint images sliding-inputted by the user;

the fingerprint sensor collects a to-be-identified fingerprint image pressing-inputted by the user, and the processing unit extracts characteristic points of the to-be-identified fingerprint image and determines whether the characteristic points of the to-be-identified fingerprint image match with the characteristic points of the template fingerprint image;

when the characteristic points of the to-be-identified fingerprint image match with the characteristic points of the template fingerprint image, the processing unit determines the to-be-identified fingerprint image as a matching fingerprint image; and when the characteristic points of the to-be-identified fingerprint image do not match with the characteristic points of the template fingerprint image, the processing unit determines the to-be-identified fingerprint image as a non-matching fingerprint image.

In one embodiment, the processing unit is configured to perform filtering, binarization, and thinning processing on the template fingerprint image, and to extract the characteristic points of the template fingerprint image.

In one embodiment, the previous frame of fingerprint images includes the previous frame image part, the current frame of fingerprint images includes a plurality of current frame image parts, and the judging unit respectively calculate gray differences between the first gray scale of the previous frame image part and corresponding second gray scales of the plurality of the current frame image parts to obtain a plurality of the gray scale differences, and to compare the plurality of the gray scale differences; and when a gray scale difference between a second gray scale and the first gray scale is a minimum gray scale difference among the plurality of the gray scale differences, and the minimum gray scale deference is smaller than a first threshold, the judging unit is configured to determine the current frame image part corresponding to the second gray scale as the first overlap region.

In one embodiment, the previous frame of fingerprint images includes the previous frame image part, the current frame of fingerprint images includes groups of a plurality of current frame image parts, and each group of the plurality of current frame image parts includes a first current frame image part, a second current frame image part, and a third current frame image part;

the judging unit is configured to calculate a first gray scale difference between a first gray scale of the previous frame image part and a first gray scale of the first current frame image part of one group of current frame image parts, a second gray scale difference between the first gray scale of the previous frame image part and a second gray scale of the second current frame image part of the one group of current frame image parts, and a third gray scale difference between the first gray scale of the previous frame image part and a third gray scale of the third current frame image part of the one group of current frame image parts, respectively, to obtain a gray scale sum of the first gray scale difference, the second gray scale difference and the third gray scale difference and, after a plurality of gray scale sums are obtained, to compare the plurality of gray scale sums;

when the gray scale sum of a group of current frame image parts has a minimum value among the plurality of the gray scale sums, the judging unit compares the first gray scale difference, the second gray scale difference, and the third gray scale difference corresponding to the one group of current frame image parts; and when a value of a gray scale difference is minimum among the group and the value is less than a second threshold, the judging unit determines the current frame image part corresponding to the gray scale difference having the minimum value as the first overlap region.

Additional aspect and advantages of the present disclosure will be partly provided in the following description, and part of the additional aspect and the advantages will become apparent from the following description, or will be know from embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
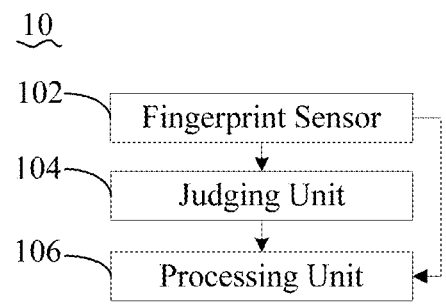
FIG. 1 is a block diagram of a fingerprint identification system according to an embodiment of the present disclosure.

Embodiments of the present disclosure are described in detail below, and examples of the embodiments are shown in accompanying drawings, wherein identical or similar marks denote identical or similar components or components with the same or similar function from beginning to end. The following embodiments described by referring to the accompanying drawings are illustrative, aim at explaining the present disclosure, and should not be interpreted as limitations to the present disclosure.

In addition, the terms such as "first" and "second" are used merely for the purpose of description, but shall not be construed as indicating or implying relative importance or implicitly indicating a number of the indicated technical feature. Hence, the feature defined with "first" and "second" may explicitly or implicitly include at least one of the features. In the description of the present disclosure, unless otherwise explicitly specifically defined, "multiple" means at least two, for example, two or three.

In the present disclosure, unless otherwise explicitly specified or defined, the terms such as "mount", "connect", "connection", and "fix" should be interpreted in a broad sense. For example, a connection may be a fixed connection, or may be a detachable connection or an integral connection; a connection may be a mechanical connection, or may be an electrical connection; a connection may be a mechanical connection, or may be an electrical connection, or may be used for intercommunication; a connection may be a direct connection, or may be an indirect connection via an intermediate medium, or may be communication between interiors of two elements or an interaction relationship between two elements, unless otherwise explicitly defined. It may be appreciated by those of ordinary skill in the art that the specific meanings of the aforementioned terms in the present disclosure can be understood depending on specific situations.

Various embodiments and examples are provided in the following description to implement different structures of the present disclosure. In order to simplify the present disclosure, certain elements and settings will be described. However, these elements and settings are only by way of example and are not intended to limit the present disclosure. In addition, reference numerals may be repeated in different examples in the present disclosure. This repeating is for the purpose of simplification and clarity and does not refer to relations between different embodiments and/or settings. Furthermore, examples of different processes and materials are provided in the present disclosure. However, it would be appreciated by those skilled in the art that other processes and/or materials may be also applied.

Referring to FIG. 1, the fingerprint identification system 10 according to the present disclosure includes a fingerprint sensor 102, a judging unit 104, and a processing unit 106.

Figure 2:
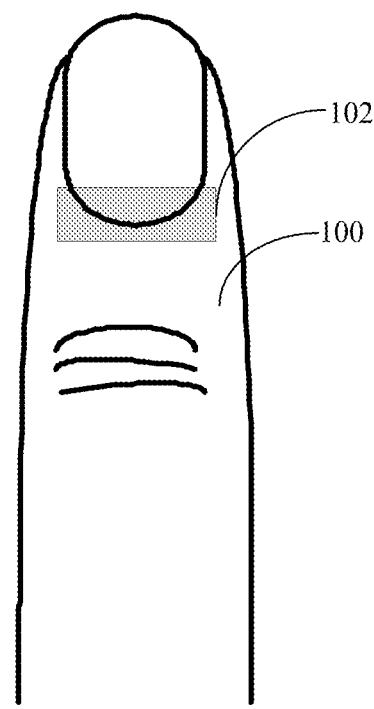
FIG. 2 is a diagram of a user inputting a fingerprint on a fingerprint sensor.

The fingerprint sensor 102 is configured to collect multiple frames of fingerprint images sliding-inputted by a user. The fingerprint sensor 102, for example, could be a surface capacitive fingerprint sensor, with a size of about 4*8 mm, 508 dpi, a resolution of about 80*160. The multiple frames of fingerprint images are inputted by the user in a sliding-input format, referring to FIG. 2, where the user slides the finger 100 through a detection panel of the fingerprint sensor 102 and, then, the fingerprint sensor 102 can collect multiple frames of sliding fingerprint images of the finger in a sequence.

The judging unit 104 is configured to judge whether, among the multiple frames of fingerprint images, there is a first overlap region between a current frame of fingerprint images and a previous frame of fingerprint images. If yes, the judging unit 104 is also configured to remove the first overlap region from the current frame of fingerprint images and to superpose the previous frame of fingerprint images with the current frame of fingerprint images without the first overlap region thereof to form a superposed fingerprint image. If no, the fingerprint sensor is configured to again collecting new multiple frames of fingerprint images sliding-inputted by the user. The judging unit 104 is also configured to judge whether there is a second overlap region between a next frame of fingerprint images and the superposed fingerprint image, until completing judgment of all the multiple frames of fingerprint images to obtain a template fingerprint image.

In certain other embodiments, the judging unit 104 can also be configured to remove the first overlap region from the previous frame of fingerprint images and to superpose the current frame of fingerprint images with the previous frame of fingerprint images without the first overlap region to form the superposed fingerprint image.

Figure 3:
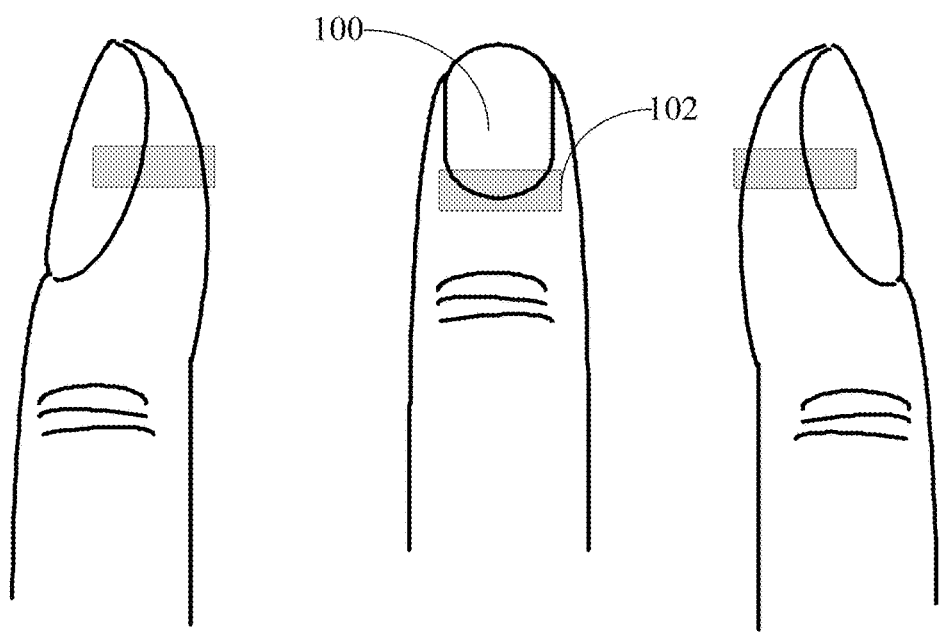
FIG. 3 is a diagram of a user inputting fingerprint at different-positions of a finger on a fingerprint sensor.

Because the area of the fingerprint sensor 102 is relatively small, and the area of the fingerprint is relatively big, when collecting the fingerprint, the fingerprint sensor 102 can collect the multiple fingerprint images frame by frame and, when two adjacent frames of fingerprint images have a part of same area, the judging unit 104 can stitch the two adjacent frames of fingerprint images as another frame of fingerprint image. Therefore, referring to FIG. 3, the left side, the middle, and the right side of the finger are respectively sliding-inputted through the detection panel of the fingerprint sensor 102 by the user. Each time the fingerprint is sliding-inputted, the judging unit 104 stitches the multiple frames of fingerprint images, which are collected by the fingerprint sensor 102, as a template fingerprint image frame, and three template fingerprint image frames can be stitched together to form a complete template fingerprint image.

Specifically, in this embodiment, the previous frame of fingerprint image includes a previous frame image part, the current frame of fingerprint images includes groups of a plurality of current frame image parts, and each group of the plurality of current frame image parts may include a first current frame image part, a second current frame image part, and a third current frame image part.

The judging unit 104 is configured to calculate a first gray scale difference between a first gray scale of the previous frame image part and a first gray scale of the first current frame image part of one group of current frame image parts, a second gray scale difference between the first gray scale of the previous frame image part and a second gray scale of the second current frame image part of the one group of current frame image parts, and a third gray scale difference between the first gray scale of the previous frame image part and a third gray scale of the third current frame image part of the one group of current frame image parts, respectively, to obtain a gray scale sum of the first gray scale difference, second gray scale difference and the third gray scale difference. After a plurality of gray scale sums are obtained, the plurality of gray scale sums are compared.

When the gray scale sum of a group of current frame image parts has a minimum value among the plurality of the gray scale sums, the judging unit 104 is configured to compare the first gray scale difference, the second gray scale difference, and the third gray scale difference corresponding to the one group of current frame image parts.

When the value of a gray scale difference is minimum among the group, and the value is less than a threshold, the judging unit 104 is configured to determine the current frame image part corresponding to the gray scale difference having the minimum value as the first overlap region. If no gray scale difference having the minimum value less than the threshold, the judging unit 104 prompts the user to again sliding-input the fingerprint image.

Figure 4:
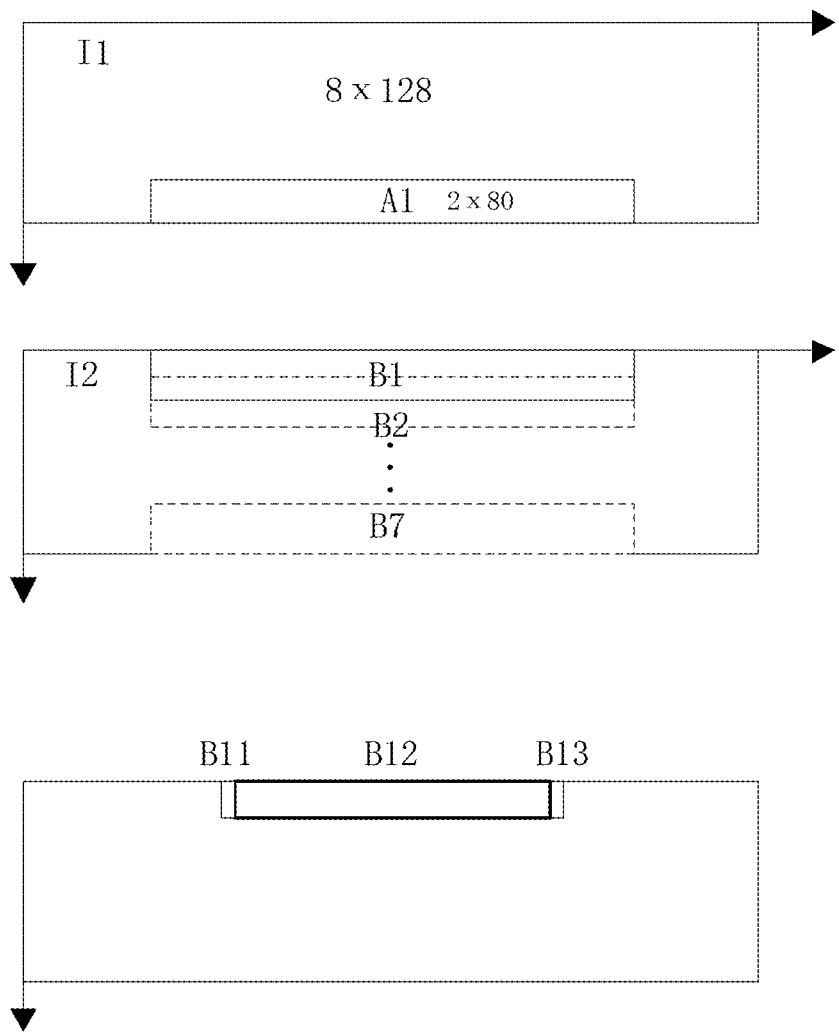
FIG. 4 is a schematic diagram of a fingerprint identification system according to an embodiment of the present disclosure.

For example, referring to FIG. 4, the previous frame of fingerprint images I1 (the resolution is 8*128) includes the previous frame image part A1 (the resolution is 2*80), the current frame of fingerprint images I2 (the resolution is 8*128) includes seven groups of current frame image parts B1-B7 (the resolution of each group of current frame image parts Bn is 2*82, n=1, 2, . . . , 7).

The previous frame image part A1 is at a center location of last two rows of the previous frame of fingerprint images I1, that is, the previous frame image part A1 is an image part from the $7^{th}$ row to the $8^{th}$ row and from the $25^{th}$ column to the $104^{th}$ column of the previous frame of fingerprint images I1.

Each group of current frame image parts Bn includes the first current frame image part Bn1, the second current frame image part Bn2, and the third current frame image part Bn3. The resolution of the first current frame image part Bn1, the second current frame image part Bn2, and the third current frame image part Bn3 is 2*80. The second current frame image part Bn2 locates at middle of the group of current frame image part Bn, and at middle of the current frame of fingerprint images I2 along a direction of resolution line. That is, the number of the resolution columns between the leftmost of the second current frame image part Bn2 and the leftmost of the current frame of fingerprint images I2 is equal to the number of the resolution columns between the rightmost of the second current frame image part Bn2 and the rightmost of the current frame of fingerprint images I2. The first current frame image part Bn1 shifts to left by one column from the second current frame image part Bn2 along the direction of the resolution line, and the third current frame image part Bn3 shifts to right by one column from the second current frame image part Bn2 along the direction of the resolution line. Thus, the shifted image parts are used to take account in the factor that the user may turn the finger left and/or turn the finger right in a process of sliding-inputting the fingerprint, such that an accuracy of fingerprint synthesis may be higher.

For example, for the group of current frame image parts B1, the group of current frame image parts B1 includes the first current frame image part B11, the second current frame image part B12, and the third current frame image part B13. The first current frame image part B11 is the image part from the row to the $2^{nd}$ row and from the $24^{th}$ column to the $103^{th}$ column of the current frame of fingerprint images I2, the second current frame image part B12 is the image part from the $1^{st}$ row to the $2^{nd}$ row and from the $25^{th}$ column to the $104^{th}$ column of the current frame, and the third current frame image part B13 is the image part from the $1^{st}$ row to the $2^{nd}$ row and from $26^{th}$ column to the $105^{th}$ column of the current frame.

For the group of current frame image parts B2, the group of current frame image parts B2 includes the first current frame image part B21, the second current frame image part B22, and the third current frame image part B23. The first current frame image part B21 is the image part from the $2^{nd}$ row to the $3^{rd}$ row and from the $24^{th}$ column to the $103^{th}$ column of the current frame, the second current frame image part B22 is the image part from the $2^{nd}$ row to the $3^{rd}$ row and from the $25^{th}$ column to the $104^{th}$ column of the current frame, and the third current frame image part B33 is the image part from the $2^{nd}$ row to the $3^{rd}$ row and from $26^{th}$ column to the $105^{th}$ column of the current frame. Other groups of current frame image parts can be similarly formed.

The judging unit 104 is configured to calculate respectively gray scale differences between the first gray scale G1 of the previous frame image part A1 and the first gray scale Gn1 of the first current frame image part Bn1, the second gray scale Gn2 of the second current frame image part Bn2, and the third gray scale Gn3 of the third current frame image part Bn3 of a same current frame image part Bn, to obtain the first gray scale difference Dn1, the second gray scale difference Dn2 and the third gray scale difference Dn3; to calculate the gray scale sum of the first gray scale difference Dn1, the second gray scale difference Dn2, and the third gray scale difference Dn3 so as to obtain a plurality of the gray scale sums Sn, and to compare the plurality of the gray scale sums Sn.

When a gray scale sum Sn corresponding to one of the plurality of groups of current frame image parts Bn is the minimum among the plurality of gray scale sums, the judging unit 104 is configured to compare the first gray scale difference Dn1, the second gray scale difference Dn2, and the third gray scale difference Dn3 corresponding to the group of current frame image parts Bn having the minimum gray scale sum.

When the minimum gray scale difference min_Dni, i=1, 2, 3, is obtained, and the minimum gray scale difference min_Dni is smaller than the threshold, the judging unit 104 is configured to determine the current frame image part Bni corresponding to the minimum gray scale difference min_Dni as the first overlap region.

Specifically, the judging unit 104 is configured to respectively calculate the gray scale differences between the first gray scale G1 and the first gray scale G11 of the first current frame image part B11, the second gray scale G12 of the second current frame image part B12, and the third gray scale G13 of the third current frame image part B13 of the group of current frame image parts B1 to obtain the first gray scale difference D11, the second gray scale difference D12 and the third gray scale difference D13, respectively, and to calculate the gray scale sum S1 of the first gray scale difference D11, the second gray scale difference D12 and the third gray scale difference D13. Similarly, the judging unit 104 calculates the gray scale sum S2 corresponding to the group of current frame image parts B2, the gray scale sum S3 corresponding to the group of current frame image parts B3, the gray scale sum S4 corresponding to the group of current frame image parts B4, the gray scale sum S5 corresponding to the group of current frame image parts B5, the gray scale sum S6 corresponding to the group of current frame image parts B6 and the gray scale sum S7 corresponding to the group of current frame image parts B7.

The judging unit 104 compares the seven gray scale sums S1, S2, . . . , S7. If the gray scale sum S1 corresponding to the group of current frame image parts B1 is the minimum value among the seven gray scale sums, the judging unit 104 further compares the first gray scale difference D11, the second gray scale difference D12, and the third gray scale difference D13 corresponding to the group of current frame image parts B1.

If it is determined that the second gray scale difference D12 is the minimum gray scale difference and, as the minimum value, the second gray scale difference D12 is smaller than the threshold, the judging unit 104 determines the current frame image part B12 corresponding to the minimum second gray scale difference D12 as the first overlap region.

The judging unit 104 removes the first overlap region B12 from the current frame of fingerprint images I2, and then superposes the current frame of fingerprint images I2 without the first overlap region B12 with the previous frame of fingerprint images I1, such that the previous frame image part A1 of the previous frame of fingerprint images I1 is located at the position where the first overlap region B12 was removed to obtain a superposed fingerprint image. The judging unit completes the determination of remaining multiple frames of fingerprint images and obtains a complete template fingerprint image.

The processing unit 106 is configured to extract and save the characteristic points of the complete template fingerprint image. The processing unit 106 performs filtering, binarization, and thinning processing on the template fingerprint image to collect characteristic point information. The processing unit 106 establishes a fingerprint template database, and the template fingerprint image in the database are used in subsequent matching processes.

In a subsequent matching process, the fingerprint sensor 102 is also configured to collect a to-be-identified fingerprint image pressing-inputted by a user. The processing unit 106 is configured to judge whether the characteristic points of the to-be-identified fingerprint image matches with the characteristic points of the template fingerprint image. If yes, the processing unit 106 is configured to determine the to-be-identified fingerprint image as the matching fingerprint image; and if no, the processing unit 106 is configured to determine the to-be-identified fingerprint image as the non-matching fingerprint image. When the collected characteristic point of the to-be-identified fingerprint image matches with the characteristic points of the template fingerprint image, the matching operation is successful.

The fingerprint identification system 10, when establishing a template fingerprint database, uses the fingerprint sensor 102 to collect the multiple frames of fingerprint images sliding-inputted by the user, and uses the judging unit 104 to superpose the sliding-inputted frames together using an image-stitching technique. Thus, the amount of information collected by the fingerprint sensor for each sliding-input is much more than the amount of information collected by the fingerprint sensor for each pressing-input under existing methods, and the input efficiency is much higher than that of existing methods. The inputting process can be completed by one-time collection of the left side, middle side, and right side of the finger, respectively, and is convenient to input, avoiding complex operations and improving user experience. It can be understood that, through a user interface such as a user interface displayed on a display screen, the fingerprint identification system 10 prompts the user for sliding-inputting fingerprint at a corresponding position of the finger 100, for example, fingerprint at the left side of the finger 100. After the fingerprint at the left side of the finger 100 is inputted successfully, the user continues to complete fingerprint-inputting of fingerprint at the right side and the middle side of the finger 100 under the prompt of the fingerprint identification system 10.

In the subsequent matching process, the user does not need to sliding-input the fingerprint and there is no image-stitching needed, but only needs to press on the detecting panel of the fingerprint sensor 102 to collect the fingerprint. That is, in the subsequent matching process, the user presses the finger on the fingerprint sensor 102, and the fingerprint sensor 102 can collect the fingerprint of the pressed-part of the finger, and the processing unit 106 can compare the collected fingerprint with template fingerprint database. It is possible that the user uses regular angles when inputting the fingerprints, but the matching process can still be successful at various angles.

Another embodiment of the present disclosure provides a fingerprint identification system. The fingerprint identification system is largely the same as the fingerprint identification system provided in the previous embodiment but with a few differences. In the present embodiment, the previous frame of fingerprint images includes a previous frame image part, the current frame of fingerprint images includes a plurality of the current frame image parts, and the judging unit is configured to respectively calculate the gray difference between the first gray scale of the previous frame image part and corresponding second gray scales of the plurality of the current frame image parts to obtain the plurality of the gray scale differences, and to compare the plurality of the gray scale differences.

When a gray scale difference between a second gray scale and the first gray scale is a minimum gray scale difference among the plurality of the gray scale differences, and the minimum gray scale deference is smaller than a threshold, the judging unit is configured to determine the current frame image part corresponding to the second gray scale as the first overlap region. If there is no minimum gray scale difference smaller than the threshold, the judging unit 104 prompts the user to again sliding-input frames of fingerprint images.

Figure 5:
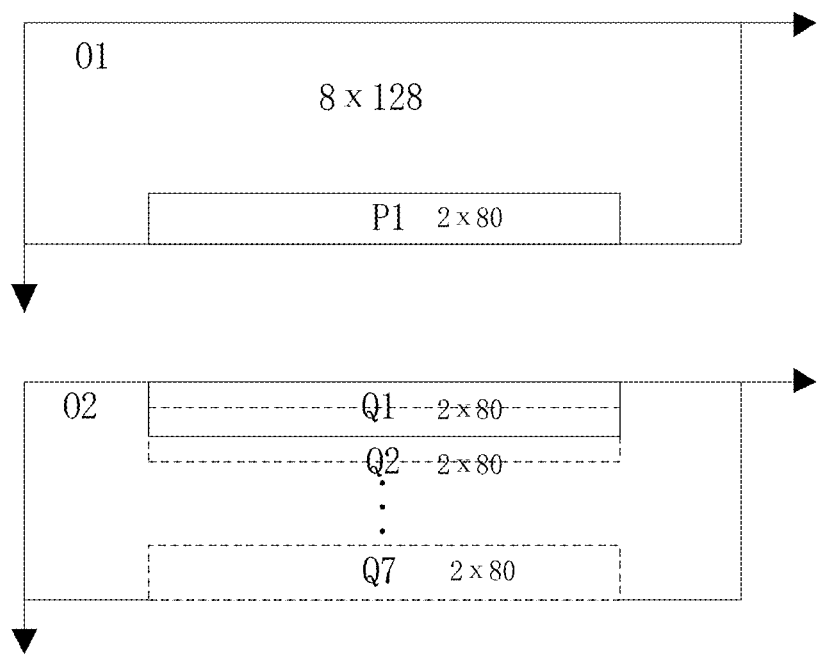
FIG. 5 is another schematic diagram of a fingerprint identification system according to an embodiment of the present disclosure.

For example, referring to FIG. 5, the previous frame of fingerprint images 01 (the resolution is 8*128) includes the previous frame image part P1 (the resolution is 2*80), the current frame of fingerprint images 02 (the resolution is 8*128) includes seven current frame image parts Qn (n=1, 2, . . . , 7).

The previous frame image part P1 is at a location of last two lines of the previous frame of fingerprint images 01, that is, the previous frame image part P1 is the image part of twenty-fifth to $104^{th}$ columns of seventh to eighth lines of the previous frame of fingerprint images 01.

The current frame image parts Qn are located at the middle of the current frame of fingerprint images 02 and along a direction of the resolution row, that is, the number of the resolution columns between the leftmost of a current frame image part Qn and the leftmost of the current frame of fingerprint images 02 is equal to the number of the resolution columns between the rightmost of the current frame image part Qn and the rightmost of the current frame of fingerprint images 02.

For example, for the current frame image part Q1, the current frame image part Q1 is the image part from the $1^{st}$ row to the $2^{nd}$ row and from the $25^{th}$ column to the $104^{th}$ column of the current frame of fingerprint images 02.

For the current frame image part Q2, the current frame image part Q2 is the image part from the $2^{nd}$ row to the $3^{rd}$ row and from the $25^{th}$ column to the $104^{th}$ column of the current frame of fingerprint images 02. Other current frame image parts may be similarly obtained.

The judging unit 104 is configured to respectively calculate the gray scale difference between the first gray scale G0 of the previous frame image part P1 and seven second gray scales Gn of the seven current frame image parts Qn to obtain seven gray scale differences Dn, and to compare the seven gray scale differences Dn.

If a gray scale difference Dn between a second gray scale Gn and the first gray scale G0 is the minimum value min_Dn among the plurality of the gray scale differences, and the minimum value min_Dn is smaller than the threshold, the judging unit is configured to determine the current frame image part Qn corresponding to the second gray scale Gn having the minimum value min_Dn as the first overlap region.

For example, if the gray scale difference D2 between the second gray scale G2 and the first gray scale G0 is the minimum value among the seven gray scale differences, and the gray scale difference D2 is smaller than the threshold, the judging unit is configured to determine the current frame image part Q2 corresponding to the second gray scale G2 as the first overlap region.

The judging unit removes the first overlap region Q2 from the current frame of fingerprint images 02, and then superposes the current frame of fingerprint images 02 without the first overlap region Q2 with the previous frame of fingerprint images 01, such that the previous frame image part P1 of the previous frame of fingerprint images 01 is located at the position where the first overlap region Q2 was removed to obtain a superposed fingerprint image. The judging unit completes the determination of remaining multiple frames of fingerprint images and obtains a complete template fingerprint image.

The fingerprint identification system according to this embodiment requires the user not to rotate the finger when sliding-inputting the fingerprint, so as to improve the inputting success rate.

Figure 6:
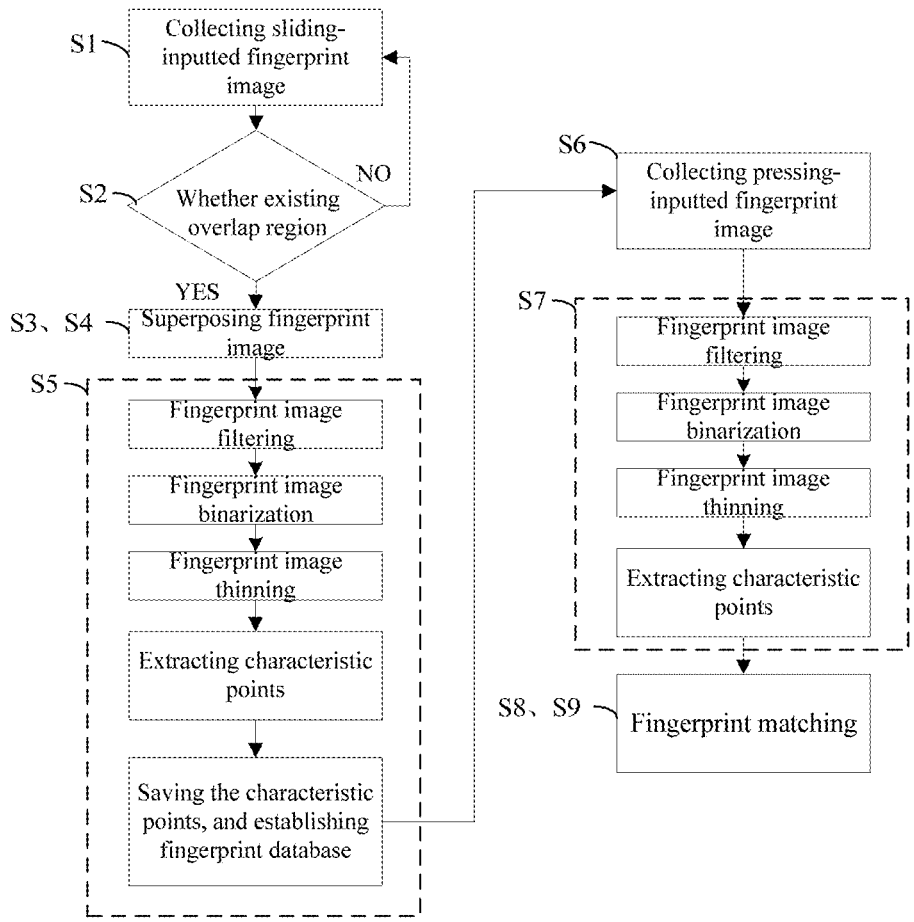
FIG. 6 is a flow diagram of a fingerprint identification method according to an embodiment of the present disclosure.

Referring to FIG. 6, a fingerprint identification method according to an embodiment of the present disclosure is provided, the method includes the followings:

S1: the fingerprint sensor collects multiple frames of fingerprint images sliding-inputted by a user.

S2: the judging unit determines whether, among the multiple frames of fingerprint images, there is a first overlap region between a current frame of fingerprint images and a previous frame of fingerprint images. If yes, the method proceeds to Step S3; if no, the method returns to Step S1.

S3: the judging unit removes the first overlap region from the current frame of fingerprint images and superposes the previous frame of fingerprint images with the current frame of fingerprint images without the first overlap region thereof to form a superposed fingerprint image; or the judging unit removes the first overlap region from the previous frame of fingerprint images and superposes the current frame of fingerprint images with the previous frame of fingerprint images without the first overlap region to form the superposed fingerprint image.

S4: the judging unit judges whether there is a second overlap region between a next frame of fingerprint images and the superposed fingerprint image, until completing judgment of all the multiple frames of fingerprint images to obtain a template fingerprint image.

S5: the processing unit extracts and saves the characteristic points of the complete template fingerprint image.

S6: the fingerprint sensor collects a to-be-identified fingerprint image pressing-inputted by the user.

S7: the processing unit extracts characteristic points of the to-be-identified fingerprint image, and determines whether the characteristic points of the to-be-identified fingerprint image match with the characteristic points of the template fingerprint image. If yes, the method proceeds to Step S8; if no, the method proceeds to Step S9.

S8: the processing unit determines the to-be-identified fingerprint image as the matching fingerprint image.

S9: the processing unit determines the to-be-identified fingerprint image as the non-matching fingerprint image.

It is understood that the above fingerprint identification method can be implemented by the fingerprint identification system. The Steps S3 and S4 can be understood as stitching steps of the fingerprint image.

In one embodiment, in Step S5, the processing unit performs filtering, binarization, and thinning processing on the template fingerprint image, and extracts the characteristic points of the template fingerprint image.

In one embodiment, in Step S2, the previous frame of fingerprint images includes the previous frame image part, the current frame of fingerprint images includes a plurality of current frame image parts, and the judging unit respectively calculates the gray difference between the first gray scale of the previous frame image part and corresponding second gray scales of the plurality of the current frame image parts to obtain the plurality of the gray scale differences, and compares the plurality of the gray scale differences.

When a gray scale difference between a second gray scale and the first gray scale is a minimum gray scale difference among the plurality of the gray scale differences, and the minimum gray scale deference is smaller than a threshold, the judging unit is configured to determine the current frame image part corresponding to the second gray scale as the first overlap region.

In one embodiment, in Step S2, the previous frame of fingerprint images includes the previous frame image part, the current frame of fingerprint images includes groups of a plurality of current frame image parts, and each group of the plurality of current frame image parts may include a first current frame image part, a second current frame image part, and a third current frame image part.

The judging unit respectively calculates a first gray scale difference between a first gray scale of the previous frame image part and a first gray scale of the first current frame image part of one group of current frame image parts, a second gray scale difference between the first gray scale of the previous frame image part and a second gray scale of the second current frame image part the one group of current frame image parts, and a third gray scale difference between the first gray scale of the previous frame image part and a third gray scale of the third current frame image part the one group of current frame image parts, respectively, to obtain a gray scale sum of the first gray scale difference, the second gray scale difference and the third gray scale difference and, after a plurality of gray scale sums are obtained, compares the plurality of gray scale sums.

When the gray scale sum of a group of current frame image parts has a minimum value among the plurality of the gray scale sums, the judging unit compares the first gray scale difference, the second gray scale difference, and the third gray scale difference corresponding to the one group of current frame image parts.

When the value of a gray scale difference is minimum among the group, and the value is less than a threshold, the judging unit determines the current frame image part corresponding to the gray scale difference having the minimum value as the first overlap region.

According to the above fingerprint identification method, when establishing the template fingerprint database, the fingerprint sensor is used to collect the multiple frames of fingerprint images sliding-inputted by the user, and the judging unit 104 superposes the sliding-inputted frames together using an image-stitching technique. Thus, the amount of information collected by the fingerprint sensor for each sliding-input is much more than the amount of information collected by the fingerprint sensor for each pressing-input under existing methods, and the input efficiency is much higher than that of existing methods. The inputting process can be completed by one-time collection of the left side, middle side, and right side of the finger, respectively, and is convenient to input, avoiding complex operations and improving user experience. In the subsequent matching process, the user presses the finger on the fingerprint sensor, and the fingerprint sensor can collect the fingerprint of the pressed-part of the finger, and the processing unit can compare the collected fingerprint with template fingerprint database. It is possible that the user uses regular angles when inputting the fingerprints, but the matching process can still be successful at various angles.

Figure 7:
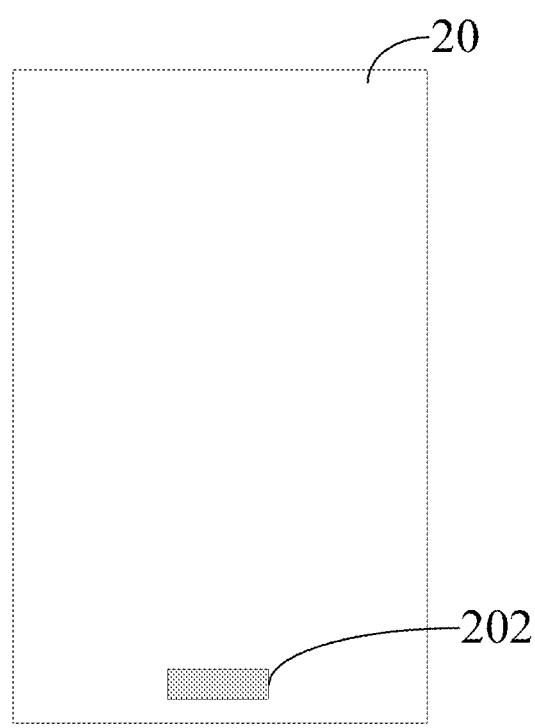
FIG. 7 is a frame diagram of an electric equipment according to an embodiment of the present disclosure.

Referring to FIG. 7, the electric equipment 20 according to embodiments of the present disclosure includes the fingerprint identification system according to any embodiment of the present disclosure. The electric equipment 20 can be a mobile phone, a tablet computer and other terminal equipment. When the fingerprint identification system is used for a mobile phone, as shown in the FIG. 2, the fingerprint sensor 202 is located on a lower Home key of an electric equipment 20, on a lateral side of the mobile phone, or on a back side of the mobile phone, etc. When the user uses the electric equipment for the first time, referring to FIG. 3, the user presses the finger on the fingerprint sensor, and respectively slides the right side of the finger, the middle side of the finger, and the right side of the finger through the fingerprint sensor 202. Thus, the characteristic points of a whole finger 100 can be recorded via sliding-inputting the fingerprint. When the user subsequently uses the electric equipment to unlock the electric equipment, the user only needs to press the finger 100 on the fingerprint sensor 202, without the need to slide the finger, the fingerprint can be successfully recognized from all angles.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

In addition, the terms such as "first" and "second" are used merely for the purpose of description, but shall not be construed as indicating or implying relative importance or implicitly indicating a number of the indicated technical feature. Hence, the feature defined with "first" and "second" may explicitly or implicitly include at least one of the features. In the description of the present disclosure, unless otherwise explicitly specifically defined, "multiple" means at least two, for example, two or three.

Any procedure or method described in the flow charts or described in any other way herein may be understood to comprise one or more modules, portions or parts for storing executable codes that realize particular logic functions or procedures. Moreover, advantageous embodiments of the present disclosure comprise other implementations in which the order of execution is different from that which is depicted or discussed, including executing functions in a substantially simultaneous manner or in an opposite order according to the related functions. This should be understood by those skilled in the art which embodiments of the present disclosure belong to.

The logic and/or step described in other manners herein or shown in the flow chart, for example, a particular sequence table of executable instructions for realizing the logical function, may be specifically achieved in any computer readable medium to be used by the instruction execution system, device or equipment (such as the system based on computers, the system comprising processors or other systems capable of obtaining the instruction from the instruction execution system, device and equipment and executing the instruction), or to be used in group with the instruction execution system, device and equipment.

It is understood that each part of the present disclosure may be realized by the hardware, software, firmware or their group. In the above embodiments, a plurality of steps or methods may be realized by the software or firmware stored in the memory and executed by the appropriate instruction execution system. For example, if it is realized by the hardware, likewise in another embodiment, the steps or methods may be realized by one or a group of the following techniques known in the art: a discrete logic circuit having a logic gate circuit for realizing a logic function of a data signal, an application-specific integrated circuit having an appropriate group logic gate circuit, a programmable gate array (PGA), a field programmable gate array (FPGA), etc.

Those skilled in the art shall understand that all or parts of the steps in the above exemplifying method of the present disclosure may be achieved by commanding the related hardware with programs. The programs may be stored in a computer readable storage medium, and the programs comprise one or a group of the steps in the method embodiments of the present disclosure when run on a computer.

In addition, each function cell of the embodiments of the present disclosure may be integrated in a processing module, or these cells may be separate physical existence, or two or more cells are integrated in a processing module. The integrated module may be realized in a form of hardware or in a form of software function modules. When the integrated module is realized in a form of software function module and is sold or used as a standalone product, the integrated module may be stored in a computer readable storage medium.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A fingerprint identification system, comprising a fingerprint sensor, a judging unit, and a processing unit, wherein:
    the fingerprint sensor collects multiple frames of fingerprint images sliding-inputted by a user, the fingerprint images are collected from a left side, a middle portion and a right side of a finger, and each of the left side, the middle portion and the right side of the finger is separately sliding-inputted through a detection panel of the fingerprint sensor;

the judging unit determines whether, among the multiple frames of fingerprint images of each of the left side, the middle portion and the right side of the finger, there is a first overlap region between a current frame of fingerprint images and a previous frame of fingerprint images;

when there is a first overlap region between the current frame of fingerprint images and the previous frame of fingerprint images, the judging unit removes the first overlap region from the current frame of fingerprint images and superposes the previous frame of fingerprint images with the current frame of fingerprint images without the first overlap region thereof to separately form a superposed fingerprint image of each of the left side, the middle portion and the right side of the finger; or the judging unit removes the first overlap region from the previous frame of fingerprint images and superposes the current frame of fingerprint images with the previous frame of fingerprint images without the first overlap region to separately form the superposed fingerprint image of each of the left side, the middle portion and the right side of the finger;

the judging unit also judges whether there is a second overlap region between a next frame of fingerprint images and the superposed fingerprint image, until completing judgment of all the multiple frames of fingerprint images of each of the left side, the middle portion and the right side of the finger to obtain three template fingerprint images collected from the left side, the middle portion and the right side of the finger, and the three template fingerprint images are stitched together to form a complete template fingerprint image;

when there is not a first overlap region between the current frame of fingerprint images and the previous frame of fingerprint images, the fingerprint sensor collects new multiple frames of fingerprint images sliding-inputted by the user;

the processing unit extracts and saves characteristic points of the complete template fingerprint image;

the fingerprint sensor collects a to-be-identified fingerprint image pressing-inputted by the user, and the processing unit extracts characteristic points of the to-be-identified fingerprint image and determines whether the characteristic points of the to-be-identified fingerprint image match with the characteristic points of the complete template fingerprint image;

when the characteristic points of the to-be-identified fingerprint image match with the characteristic points of the complete template fingerprint image, the processing unit determines the to-be-identified fingerprint image as a matching fingerprint image; and when the characteristic points of the to-be-identified fingerprint image do not match with the characteristic points of the complete template fingerprint image, the processing unit determines the to-be-identified fingerprint image as a non-matching fingerprint image.

2. The fingerprint identification system according to claim 1, wherein the processing unit is configured to perform filtering, binarization, and thinning processing on the complete template fingerprint image, and to extract the characteristic points of the complete template fingerprint image.

3. The fingerprint identification system according to claim 1, wherein:

the previous frame of fingerprint images includes a previous frame image part, the current frame of fingerprint images includes a plurality of current frame image parts, and the judging unit respectively calculates gray differences between a first gray scale of the previous frame image part and corresponding second gray scales of the plurality of the current frame image parts to obtain a plurality of the gray scale differences, and compares the plurality of the gray scale differences; and when a gray scale difference between a second gray scale and the first gray scale is a minimum gray scale difference among the plurality of the gray scale differences, and the minimum gray scale deference is smaller than a first threshold, the judging unit is configured to determine the current frame image part corresponding to the second gray scale as the first overlap region.

4. The fingerprint identification system according to claim 1, wherein:

the previous frame of fingerprint images includes the previous frame image part, the current frame of fingerprint images includes groups of a plurality of current frame image parts, and each group of the plurality of current frame image parts includes a first current frame image part, a second current frame image part, and a third current frame image part;

the judging unit is configured to calculate a first gray scale difference between a first gray scale of the previous frame image part and a first gray scale of the first current frame image part of one group of current frame image parts, a second gray scale difference between the first gray scale of the previous frame image part and a second gray scale of the second current frame image part the one group of current frame image parts, and a third gray scale difference between the first gray scale of the previous frame image part and a third gray scale of the third current frame image part the one group of current frame image parts, respectively, to obtain a gray scale sum of the first gray scale difference, the second gray scale difference and the third gray scale difference and, after a plurality of gray scale sums are obtained, to compare the plurality of gray scale sums;

when the gray scale sum of a group of current frame image parts has a minimum value among the plurality of the gray scale sums, the judging unit compares the first gray scale difference, the second gray scale difference, and the third gray scale difference corresponding to the one group of current frame image parts; and when a value of a gray scale difference is minimum among the group and the value is less than a second threshold, the judging unit determines the current frame image part corresponding to the gray scale difference having the minimum value as the first overlap region.

5. A method of fingerprint identification, comprising:

S1: collecting, by a fingerprint sensor, multiple frames of fingerprint images sliding-inputted by a user, wherein the fingerprint images are collected from a left side, a middle portion and a right side of a finger, and each of the left side, the middle portion and the right side of the finger is separately sliding-inputted through a detection panel of the fingerprint sensor;

S2: judging, by a judging unit, whether, among the multiple frames of fingerprint images of each of the left side, the middle portion and the right side of the finger, there is a first overlap region between a current frame of fingerprint images and a previous frame of fingerprint images; when there is a first overlap region between the current frame of fingerprint images and the previous frame of fingerprint images, proceeding to S3; and when there is not a first overlap region between the current frame of fingerprint images and the previous frame of fingerprint images, returning to S1;

S3: removing, by the judging unit, the first overlap region from the current frame of fingerprint images and superposing the previous frame of fingerprint images with the current frame of fingerprint images without the first overlap region thereof to separately form a superposed fingerprint image of each of the left side, the middle portion and the right side of the finger; or removing, by the judging unit, the first overlap region from the previous frame of fingerprint images and superposing the current frame of fingerprint images with the previous frame of fingerprint images without the first overlap region to separately form the superposed fingerprint image of each of the left side, the middle portion and the right side of the finger;

S4: judging, by the judging unit, whether there is a second overlap region between a next frame of fingerprint images and the superposed fingerprint image, until completing judgment of all the multiple frames of fingerprint images of each of the left side, the middle portion and the right side of the finger to obtain three template fingerprint images collected from the left side, the middle portion and the right side of the finger, and the three template fingerprint images are stitched together to form a complete template fingerprint image;

S5: extracting and saving, by a processing unit, characteristic points of the complete template fingerprint image;

S6: collecting, by the fingerprint sensor, a to-be-identified fingerprint image pressing-inputted by the user;

S7: extracting, by the processing unit, characteristic points of the to-be-identified fingerprint image and determining whether the characteristic points of the to-be-identified fingerprint image match with the characteristic points of the complete template fingerprint image; when the characteristic points of the to-be-identified fingerprint image match with the characteristic points of the complete template fingerprint image, proceeding to S8; and when the characteristic points of the to-be-identified fingerprint image do not match with the characteristic points of the complete template fingerprint image, proceeding to S9;

S8: determining, by the processing unit, the to-be-identified fingerprint image as a matching fingerprint image; and S9: determining, by the processing unit, the to-be-identified fingerprint image as a non-matching fingerprint image.

6. The method of fingerprint identification according to claim 5, wherein Step S5 further comprises:
performing, by the processing unit filtering, binarization, and thinning processing on the complete template fingerprint image to extract the characteristic points of the complete template fingerprint image.

7. The method of fingerprint identification according to claim 5, wherein:
the previous frame of fingerprint images includes the previous frame image part, the current frame of fingerprint images includes a plurality of current frame image parts, and
Step S2 further comprises:
respectively calculating, by the judging unit, gray differences between the first gray scale of the previous frame image part and corresponding second gray scales of the plurality of the current frame image parts to obtain a plurality of the gray scale differences, and comparing the plurality of the gray scale differences; and when a gray scale difference between a second gray scale and the first gray scale is a minimum gray scale difference among the plurality of the gray scale differences, and the minimum gray scale deference is smaller than a first threshold, determining, by the judging unit, the current frame image part corresponding to the second gray scale as the first overlap region.

8. The method of fingerprint identification according to claim 5, wherein:
the previous frame of fingerprint images includes the previous frame image part, the current frame of fingerprint images includes groups of a plurality of current frame image parts, and each group of the plurality of current frame image parts includes a first current frame image part, a second current frame image part, and a third current frame image part; and
Step S2 further comprises:
calculating, by the judging unit, a first gray scale difference between a first gray scale of the previous frame image part and a first gray scale of the first current frame image part of one group of current frame image parts, a second gray scale difference between the first gray scale of the previous frame image part and a second gray scale of the second current frame image part the one group of current frame image parts, and a third gray scale difference between the first gray scale of the previous frame image part and a third gray scale of the third current frame image part the one group of current frame image parts, respectively, to obtain a gray scale sum of the first gray scale difference, the second gray scale difference and the third gray scale difference and, after a plurality of gray scale sums are obtained, comparing the plurality of gray scale sums;

when the gray scale sum of a group of current frame image parts has a minimum value among the plurality of the gray scale sums, comparing, by the judging unit, the first gray scale difference, the second gray scale difference, and the third gray scale difference corresponding to the one group of current frame image parts; and when a value of a gray scale difference is minimum among the group and the value is less than a second threshold, determining, by the judging unit, the current frame image part corresponding to the gray scale difference having the minimum value as the first overlap region.

9. An electric equipment, comprising:
a fingerprint identification system, comprising a fingerprint sensor, a judging unit, and a processing unit, wherein:
the fingerprint sensor collects multiple frames of fingerprint images sliding-inputted by a user, the fingerprint images are collected from a left side, a middle portion and a right side of a finger, and each of the left side, the middle portion and the right side of the finger is separately sliding-inputted through a detection panel of the fingerprint sensor;
the judging unit determines whether, among the multiple frames of fingerprint images of each of the left side, the middle portion and the right side of the finger, there is a first overlap region between a current frame of fingerprint images and a previous frame of fingerprint images;

when there is a first overlap region between the current frame of fingerprint images and the previous frame of fingerprint images, the judging unit removes the first overlap region from the current frame of fingerprint images and superposes the previous frame of fingerprint images with the current frame of fingerprint images without the first overlap region thereof to separately form a superposed fingerprint image of each of the left side, the middle portion and the right side of the finger; or the judging unit removes the first overlap region from the previous frame of fingerprint images and superposes the current frame of fingerprint images with the previous frame of fingerprint images without the first overlap region to separately form the superposed fingerprint image of each of the left side, the middle portion and the right side of the finger;

the judging unit also judges whether there is a second overlap region between a next frame of fingerprint images and the superposed fingerprint image, until completing judgment of all the multiple frames of fingerprint images of each of the left side, the middle portion and the right side of the finger to obtain three template fingerprint images collected from the left side, the middle portion and the right side of the finger, and the three template fingerprint images are stitched together to form a complete template fingerprint image;

the processing unit extracts and saves characteristic points of the complete template fingerprint image;

when there is not a first overlap region between the current frame of fingerprint images and the previous frame of fingerprint images, the fingerprint sensor collects new multiple frames of fingerprint images sliding-inputted by the user;

the fingerprint sensor collects a to-be-identified fingerprint image pressing-inputted by the user, and the processing unit extracts characteristic points of the to-be-identified fingerprint image and determines whether the characteristic points of the to-be-identified fingerprint image match with the characteristic points of the complete template fingerprint image;

when the characteristic points of the to-be-identified fingerprint image match with the characteristic points of the complete template fingerprint image, the processing unit determines the to-be-identified fingerprint image as a matching fingerprint image; and when the characteristic points of the to-be-identified fingerprint image do not match with the characteristic points of the complete template fingerprint image, the processing unit determines the to-be-identified fingerprint image as a non-matching fingerprint image.

10. The electric equipment according to claim 9, wherein the processing unit is configured to perform filtering, binarization, and thinning processing on the complete template fingerprint image, and to extract the characteristic points of the complete template fingerprint image.

11. The electric equipment according to claim 9, wherein the previous frame of fingerprint images includes the previous frame image part, the current frame of fingerprint images includes a plurality of current frame image parts, and the judging unit respectively calculates gray differences between the first gray scale of the previous frame image part and corresponding second gray scales of the plurality of the current frame image parts to obtain a plurality of the gray scale differences, and compares the plurality of the gray scale differences; and when a gray scale difference between a second gray scale and the first gray scale is a minimum gray scale difference among the plurality of the gray scale differences, and the minimum gray scale deference is smaller than a first threshold, the judging unit is configured to determine the current frame image part corresponding to the second gray scale as the first overlap region.

12. The electric equipment according to claim 9, wherein the previous frame of fingerprint images includes the previous frame image part, the current frame of fingerprint images includes groups of a plurality of current frame image parts, and each group of the plurality of current frame image parts includes a first current frame image part, a second current frame image part, and a third current frame image part;

the judging unit is configured to calculate a first gray scale difference between a first gray scale of the previous frame image part and a first gray scale of the first current frame image part of one group of current frame image parts, a second gray scale difference between the first gray scale of the previous frame image part and a second gray scale of the second current frame image part one group of current frame image parts, and a third gray scale difference between the first gray scale of the previous frame image part and a third gray scale of the third current frame image part, respectively, to obtain a gray scale sum of the first gray scale difference, the second gray scale difference and the third gray scale difference and, after a plurality of gray scale sums are obtained, to compare the plurality of gray scale sums;

when the gray scale sum of a group of current frame image parts has a minimum value among the plurality of the gray scale sums, the judging unit compares the first gray scale difference, the second gray scale difference, and the third gray scale difference corresponding to the group of current frame image parts; and when a value of a gray scale difference is minimum among the group and the value is less than a second threshold, the judging unit determines the current frame image part corresponding to the gray scale difference having the minimum value as the first overlap region.

* * * * *